(12) United States Patent
Edwards et al.

(10) Patent No.: US 9,905,124 B2
(45) Date of Patent: Feb. 27, 2018

(54) WIRELESS COMMUNICATION SYSTEM (71) Applicant: ROLLS-ROYCE PLC, London (GB)

(72) Inventors: Huw L Edwards, Derby (GB); Max C Y Ong, Dalkeith (AU); Haydn A Thompson, Sheffield (GB); Graham Watson, Derby (GB)

(73) Assignee: ROLLS-ROYCE plc, London (GB)

( * ) Notice: Subject to any disclaimer, the term of this patent is extended or adjusted under 35 U.S.C. 154(b) by 0 days.

(21) Appl. No.: 14/730,990

(22) Filed: Jun. 4, 2015

(65) Prior Publication Data
US 2015/0379867 A1 Dec. 31, 2015

(30) Foreign Application Priority Data

Jun. 26, 2014 (GB) .................... 1411342.7

(51) Int. Cl.
| | |
|---|---|
| *F01B 25/00* | (2006.01) |
| *G08C 17/02* | (2006.01) |
| *H04B 13/00* | (2006.01) |
| *G01N 22/00* | (2006.01) |
| *H01P 3/12* | (2006.01) |
| *B63H 5/125* | (2006.01) |

(52) U.S. Cl.
CPC ............. *G08C 17/02* (2013.01); *B63H 5/125* (2013.01); *G01N 22/00* (2013.01); *H01P 3/122* (2013.01); *H04B 13/00* (2013.01); *B63H 2005/1256* (2013.01)

(58) Field of Classification Search
CPC . F01B 25/00; H04Q 9/00; G01V 3/10; G01V 3/104; G01V 3/15; G01V 3/165; G01V 3/12; G01V 3/26; G01V 3/08; G01V 3/081; G01V 3/17; G01V 3/30; G01V 3/38; G01V 11/00; G01V 3/107
USPC ...... 324/754.06, 84, 95, 314, 329, 332, 637, 324/344, 76.26
See application file for complete search history.

(56) References Cited

U.S. PATENT DOCUMENTS

| | | | |
|---|---|---|---|
| 4,012,689 A | 3/1977 | Cox et al. | |
| 4,485,869 A | 12/1984 | Sresty et al. | |
| 5,076,397 A * | 12/1991 | Yamada | ................... F01M 1/26 123/196 S |
| 5,994,984 A | 11/1999 | Stancil et al. | |

(Continued)

FOREIGN PATENT DOCUMENTS

| | | |
|---|---|---|
| CN | 201369064 Y | 12/2009 |
| EP | 1 939 975 A1 | 7/2008 |

(Continued)

OTHER PUBLICATIONS

Nov. 20, 2015 Extended Search Report in European Patent Application No. 15170711.4.

(Continued)

*Primary Examiner* — Jermele M Hollington
*Assistant Examiner* — Taqi Nasir
(74) *Attorney, Agent, or Firm* — Oliff PLC (57) ABSTRACT

There is provided a wireless communication system for a marine propulsor, comprising: a transmitter; a receiver; and a waveguide, arranged to convey an electromagnetic data signal between the transmitter and the receiver; wherein the waveguide comprises an electrically non-conductive solid or liquid medium for propagating the electromagnetic data signal.

19 Claims, 6 Drawing Sheets

(56) References Cited

U.S. PATENT DOCUMENTS

| | | | |
|---|---|---|---|
| 6,043,505 A * | 3/2000 | Ames | G01N 21/534 250/225 |
| 6,077,400 A | 6/2000 | Kartchner | |
| 7,339,657 B2 * | 3/2008 | Coates | G01N 21/31 250/339.12 |
| 2005/0001721 A1 | 1/2005 | Houston et al. | |
| 2006/0087325 A1 * | 4/2006 | Ariav | A61B 5/02444 324/637 |
| 2010/0127892 A1 * | 5/2010 | Wesselink | H04Q 9/00 340/870.07 |
| 2011/0018734 A1 | 1/2011 | Varveropoulos et al. | |
| 2011/0144851 A1 * | 6/2011 | Gremminger | G01N 27/221 701/31.4 |
| 2011/0267603 A1 * | 11/2011 | Shaw | G01N 21/431 356/128 |
| 2012/0079830 A1 * | 4/2012 | Rodriguez | F01D 17/02 60/772 |
| 2013/0033702 A1 * | 2/2013 | Tunheim | G01N 21/85 356/73 |
| 2014/0106665 A1 * | 4/2014 | Ong | H01Q 1/007 455/14 |
| 2014/0247060 A1 * | 9/2014 | Ben Haim | G01N 27/00 324/637 |
| 2014/0327347 A1 | 11/2014 | Rebele et al. | |

FOREIGN PATENT DOCUMENTS

| | | |
|---|---|---|
| KR | 20090004545 A | 1/2009 |
| KR | 100959827 B1 | 5/2010 |
| WO | 2007/076039 A2 | 7/2007 |
| WO | 2008060150 A1 | 5/2008 |
| WO | 2008/109929 A1 | 9/2008 |
| WO | 2009/080449 A1 | 7/2009 |
| WO | 2011/153496 A1 | 12/2011 |

OTHER PUBLICATIONS

Jan. 29, 2015 Search Report issued in Application No. GB1411342.7.

Nikitin et al. "Propagation Model for the HVAC Duct as a Communication Channel," IEEE Transactions on Antennas and Propagation, vol. 51, No. 5, pp. 945-951, 2013.

Dec. 21, 2016 Office Action issued in European Application No. 15 170 711.4-1874.

* cited by examiner

WIRELESS COMMUNICATION SYSTEM

The present invention relates to a wireless communication system.

In engineering applications in many industries, there is a need to communicate data concerning the condition of a machine or its components. Examples include various types of power plants used in aircraft, motor vehicles, marine vessels, and power generation. Such machines typically comprise sensors for detecting parameters such as speed of moving components, vibration, oil pressure, temperature, and the like. The sensors are connected to a telemetry system which communicates the detected parameters for analysis and use by the operator. In particular, the data may enable the operator to anticipate potential component failures and plan maintenance schedules.

In some applications, communicating the data is difficult due to the environmental conditions. An example of a challenging environment is a marine azimuth thruster. This type of marine propulsor is mounted to the hull of a vessel below the waterline and rotates 360 degrees around the vertical axis in order to propel and steer the vessel. The internal structure of the thruster includes metal walls or bulkheads which divide the thruster into compartments that contain, among other components, machinery for driving the thruster's propeller. These compartments may be filled with oil for lubricating and cooling the drive machinery.

The thruster may be equipped with a condition monitoring system for determining the health of the thruster. Such a system typically comprises sensors and telemetry equipment, connected by wiring which is routed around the internal structure of the thruster. That is, the wires pass through the metal bulkheads and the oil. This wiring arrangement is undesirable because it is complex, time-consuming and expensive to install. A robust and reliable means of data communication is important because the thruster is required to operate reliably for extended periods, typically of about five to seven years, without servicing or repair.

For this reason it would be preferable to have a wireless communication system which could convey data signals through the internal structure of the thruster. More generally, it would be desirable to have a wireless communication system which could convey data signals through the internal structures of machines which comprise physical obstructions such as metal walls and may contain oil or other liquids. While wireless communication systems are commonly used to transfer information between two or more points which are not connected by an electrical conductor such as a wire (e.g. using radio waves, light, sound, magnetic or electric fields), these are generally designed to propagate signals through free air and are not suited to conveying data through metal walls and liquids.

It is an object of the present invention to provide a wireless communication system which alleviates the problems of the prior art at least to some extent.

The invention is set out in the accompanying claims.

According to an aspect, there is provided a wireless communication system for a marine propulsor, comprising: a transmitter; a receiver; and a waveguide, arranged to convey an electromagnetic data signal between the transmitter and the receiver; wherein the waveguide comprises an electrically non-conductive solid or liquid medium for propagating the electromagnetic data signal.

By using an electrically non-conductive solid or liquid as a propagation medium for an electromagnetic (EM) data signal, it becomes possible to utilise an existing (possibly modified) component of a marine propulsor to serve as a waveguide for conveying data through the propulsor. For example, a drive shaft of the propulsor may be adapted to form the waveguide. Alternatively, suitable waveguides may be provided by oil pipes or fuel pipes in the propulsor.

The skilled reader will understand that the term "electrically non-conductive" as used herein is intended to include media which are substantially electrically-non conductive and media having relatively low conductivity, for example, but not limited to, conductivity in the 10's to 1,000's of pico-Siemens per meter. A medium having non- or low electrical conductivity is selected because, in general, a signal will be rapidly attenuated in a medium having high electrical conductivity, thereby degrading the strength and/or quality of the signal.

The utilisation of existing structure enables communication between sensors, controllers, actuators, or other electronic devices without the need for additional wiring or cabling, thereby reducing complexity and cost. Furthermore, a waveguide is an exceptionally reliable transmission system because the "pipe" structure acts as a Faraday cage, preventing interference of, and by, the EM signal travelling there through. In turn, the reduced interference means that the communication system can operate at a lower power level, which is an important consideration for a marine propulsor where the power available may be very limited. Also, with less interference, more data can be sent. Given that the protocol overheads requirement for error management can be up to 50% of the bandwidth, this is very desirable.

The electrically non-conductive medium may be a liquid comprising an oil, a grease, a gel, a foam, or a fuel, for example a hydrocarbon fuel.

The electromagnetic data signal may comprise raw or processed sensor data, control data, or network data. The electromagnetic data signal may be a radio frequency signal or a microwave frequency signal.

The waveguide may be configured for multi-mode wave propagation. The waveguide may be configured for single-mode wave propagation.

The receiver and the transmitter may be disposed at least partially in the waveguide. Or, one of the receiver and the transmitter may be disposed at least partially in the waveguide and the other of the receiver and the transmitter may be disposed out of the waveguide. Or, the receiver and the transmitter may be disposed out of the waveguide.

The waveguide may be constructed from a metal or a metal alloy.

The waveguide may have a generally circular cross-section. Or, the waveguide may have a generally rectangular cross-section.

The waveguide may have a length in the range of about 0.1 to 10 meters. The waveguide may have a diameter or width in the range of about 30 to 100 millimeters.

One or both of the receiver and the transmitter may be integrally formed with the waveguide.

The waveguide may further comprise an electrically non-conductive gas medium, the electromagnetic data signal being conveyable through both the electrically non-conductive gas medium and the electrically non-conductive solid or liquid medium.

The wireless communication system may include a thermoelectric generator which is configured to power the wireless communication system. The thermoelectric generator may be configured to generate power using a temperature difference between a liquid inside the marine propulsor and water outside the marine propulsor. The liquid inside the marine propulsor may be of the same type as the electrically non-conductive liquid medium for conveying the electromagnetic data signal.

The wireless communication system may include a sensor which is configured to detect a physical parameter of the marine propulsor, the electromagnetic data signal corresponding to the physical parameter. The sensor may be a vibration sensor.

The waveguide may have a minimum diameter or width of about 410 millimeters and the electromagnetic data signal may have a frequency of about 443 MHz. Or, the waveguide may have a minimum diameter or width of about 210 millimeters and the electromagnetic data signal may have a frequency of about 900 MHz. Or, the waveguide may have a minimum diameter or width of about 74 millimeters and the electromagnetic data signal may have a frequency of about 2.5 GHz. Or, the waveguide may have a minimum diameter or width of about 35 millimeters and the electromagnetic data signal may have a frequency of about 5 GHz.

The waveguide may comprise the interior of a drive shaft of the marine propulsor. Or, the waveguide may comprise a tube which surrounds at least a portion of a drive shaft of the marine propulsor.

The wireless communication system may include a re-radiating element for bridging around an obstacle or a space in the propulsor to convey the electromagnetic data signal.

The wireless communication system may include an EMI choke for filtering the electromagnetic data signal.

According to another aspect, there is provided a marine propulsor, comprising a wireless communication system as described herein above.

According to another aspect, there is provided a marine propulsor comprising a wireless communication system, the wireless communication system comprising: a transmitter; a receiver; and a waveguide, arranged to convey an electromagnetic data signal between the transmitter and the receiver; wherein the waveguide comprises an electrically non-conductive solid or liquid medium for propagating the electromagnetic data signal.

The waveguide may comprise a conventional liquid-containing component of the marine propulsor, for example an oil pipe or a fuel pipe.

According to another aspect, there is provided a wireless communication system for a gas turbine engine, comprising: a transmitter; a receiver; and a waveguide, arranged to convey an electromagnetic data signal between the transmitter and the receiver; wherein the waveguide comprises an electrically non-conductive solid or liquid medium for propagating the electromagnetic data signal.

According to another aspect, there is provided a gas turbine engine comprising a wireless communication system, the wireless communication system comprising: a transmitter; a receiver; and a waveguide, arranged to convey an electromagnetic data signal between the transmitter and the receiver; wherein the waveguide comprises an electrically non-conductive solid or liquid medium for propagating the electromagnetic data signal.

The waveguide may comprise a conventional liquid-containing component of the gas turbine engine, for example an oil pipe or a fuel pipe.

According to another aspect, there is provided a wireless communication system for a marine propulsor, comprising: a transmitter; a receiver; and a waveguide, arranged to convey an electromagnetic data signal between the transmitter and the receiver; wherein the waveguide comprises an electrically non-conductive solid medium for propagating the electromagnetic data signal.

According to another aspect, there is provided a wireless communication system for a marine propulsor, comprising: a transmitter; a receiver; and a waveguide, arranged to convey an electromagnetic data signal between the transmitter and the receiver; wherein the waveguide comprises an electrically non-conductive liquid medium for propagating the electromagnetic data signal.

According to another aspect, there is provided a method of operating a wireless communication system as described herein above, the method comprising: determining dielectric properties of the solid or liquid medium; propagating the electromagnetic data signal; and adapting protocol, frequency and/or channels to suit the dielectric properties in order to optimise the quality of the electromagnetic data signal.

According to another aspect, there is provided a method of determining a change in the quality of an oil in a marine propulsor, comprising the steps: providing a marine propulsor with a wireless communication system, comprising: a transmitter; a receiver; and a waveguide, arranged to convey an electromagnetic data signal between the transmitter and the receiver; wherein the waveguide comprises an electrically non-conductive oil for propagating the electromagnetic data signal; monitoring the power required to convey the electromagnetic data signal; and identifying a change in the required power which is indicative of a change in the quality of the oil.

Embodiments will now be described, by way of example, with reference to the accompanying figures in which.

Figure 1:
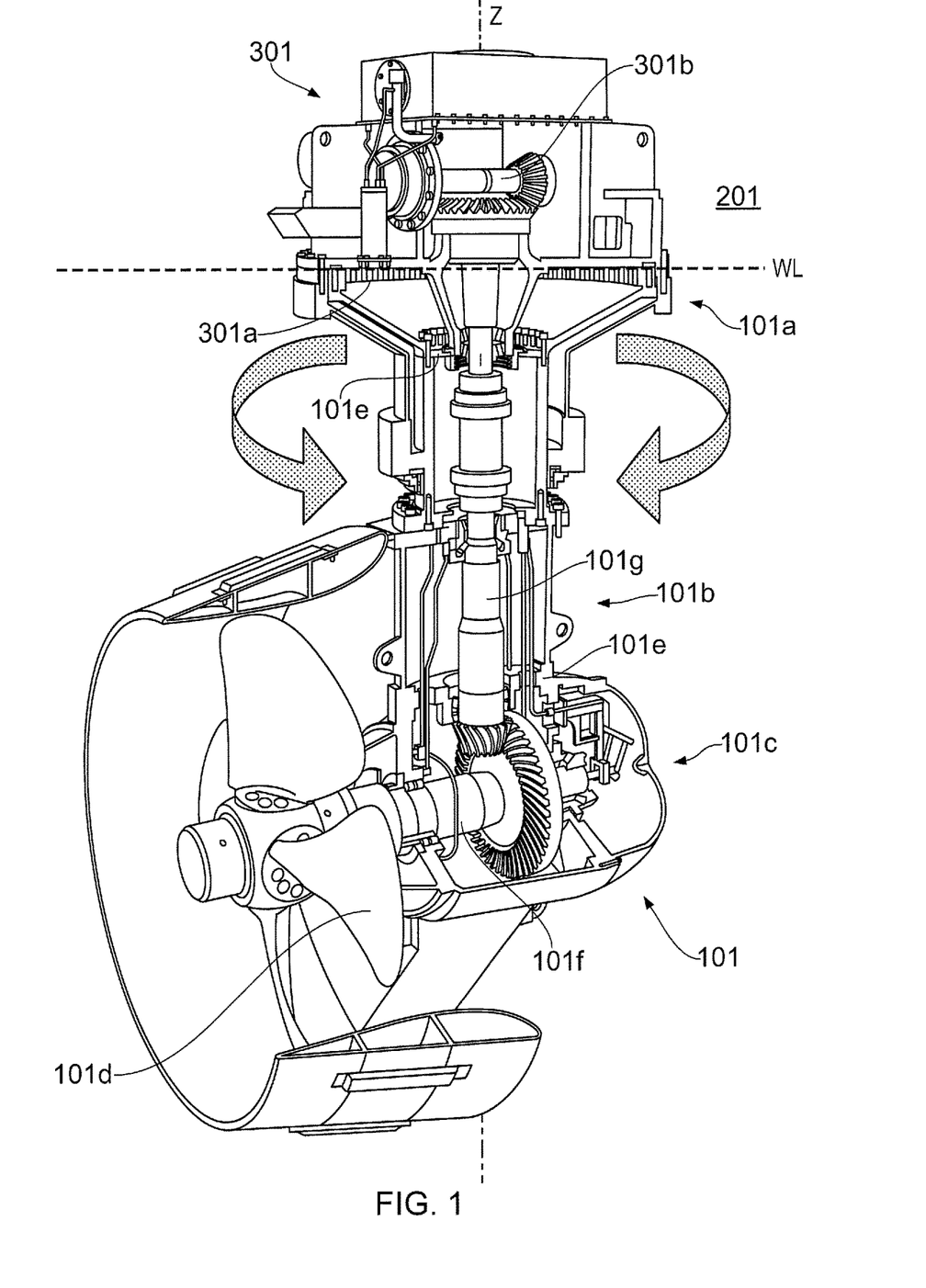
FIG. 1 is a sectional view of a marine azimuth thruster.

Referring to FIG. 1, a conventional azimuth thruster 101 is mounted to the hull 201 of a marine vessel. With the vessel in the water, most of the thruster 101 is submerged below the water line WL. The thruster 101 comprises an upper portion 101a for mounting to the hull 201, a generally elongate middle portion 101b which defines a longitudinal (vertical) axis Z of the thruster 101, and a lower portion 101c which includes a propeller 101d. Here, the upper and lower portions 101a, 101c are separated from the middle portion 101b by internal dividing structural walls, or bulkheads 101e. Thus the upper, lower and middle portions 101a-c comprise thruster chambers or compartments which contain oil (not shown) for lubrication and/or cooling of the drive mechanisms of the thruster 101, which will now be described.

The upper portion 101a of the thruster 101 includes a gear compartment 301, which is located in the hull 201 and is in fixed relationship there with. The upper portion 101a is further provided with a rotative coupling 301a, comprising a bearing and a steering gear arrangement, which divides the upper portion 101a into a fixed or stationary section (shown above the water line WL in FIG. 1 and including the gear compartment 301) and a movable section (shown below the water line WL in FIG. 1).

The propeller 101d is connected to an horizontal output shaft 101f which is disposed in the lower portion 101c of the thruster 101 and which takes its drive, via a lower bevel gear, from a lower end of a vertical drive shaft 101g which extends through the middle portion 101b (along the vertical axis Z) of the thruster 101 and through the bulkheads 101e. An upper end of the vertical drive shaft 101g extends through the rotative coupling 301a and is driven, via an upper bevel gear, by an horizontal input shaft 301b which is disposed in the gear compartment 301. In this embodiment, the horizontal input shaft 301b is driven by a diesel engine (not shown) which is disposed in the hull 201 of the vessel. In the art of marine propulsors this arrangement of horizontal and vertical shafts is sometimes referred to as a 'Z-drive'.

Thus the thruster 101 may be rotated about its vertical axis Z, relative to the hull 201, in order to provide accurate manoeuvring of the vessel. The rotation of the thruster 101 may be automatically or manually controlled, for example from the bridge of the vessel.

Figure 2:
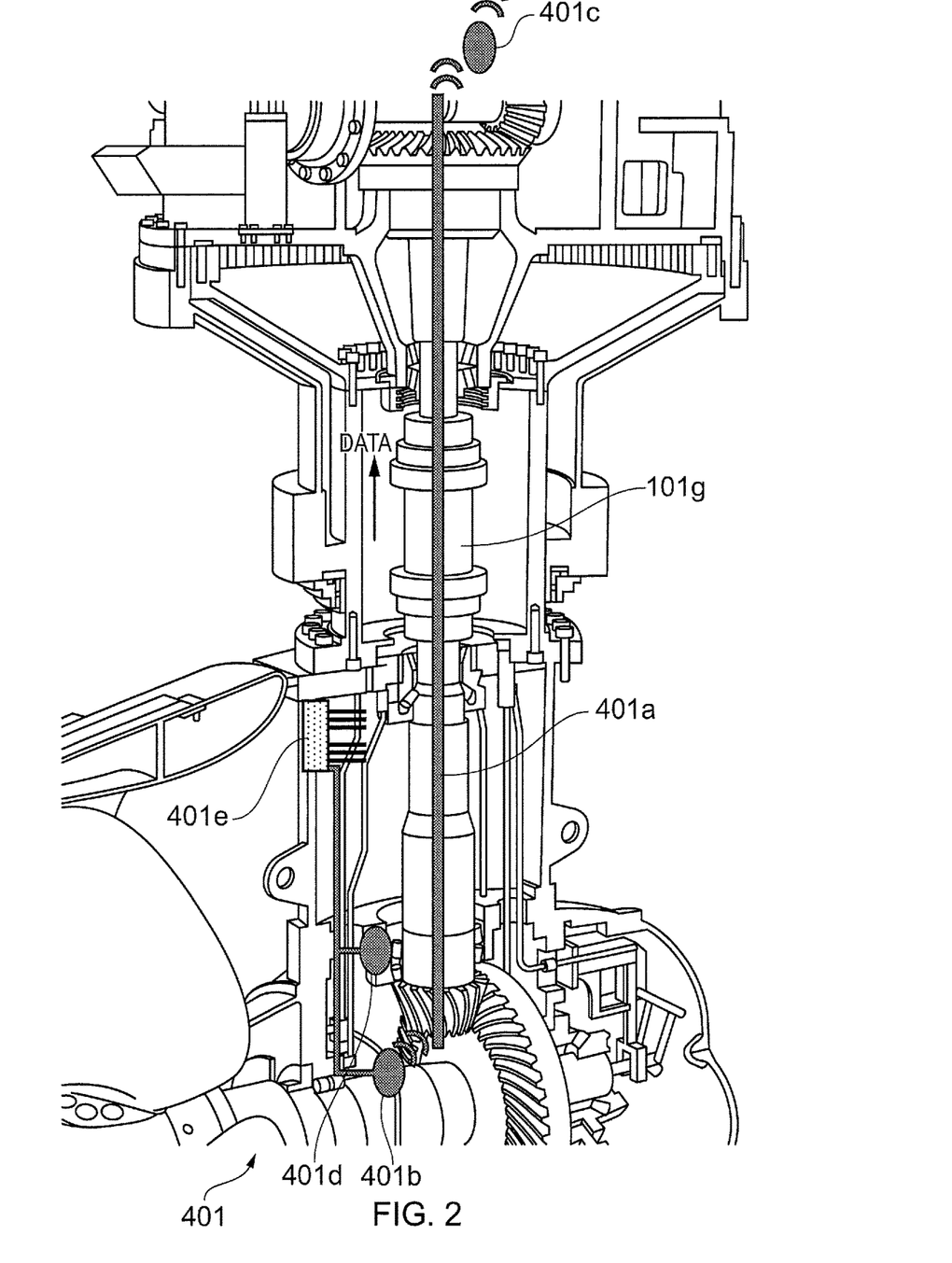
FIG. 2 shows a wireless communication system installed in the thruster of FIG. 1.

Referring now to FIG. 2, the thruster 101 is equipped with a wireless communication system 401 in accordance with the present invention. In this embodiment, the vertical drive shaft 101g is hollow (tubular) and its interior comprises a waveguide 401a having a generally circular cross-section. The waveguide 401a may have a length of about 0.5 to 5 meters, depending on the thruster type. The internal diameter of the waveguide 401a may be about 30 to 100 millimeters, depending on the frequency selected (e.g. 2.4, 5 GHz). In this embodiment, the vertical drive shaft 101g (and the waveguide 401a) is constructed from steel. In this embodiment, the interior of the waveguide 401a holds an electrically non-conductive liquid (not shown) that is capable of carrying (propagating) an electromagnetic data signal. The term "liquid" as used herein is intended to encompass all fluids which exhibit liquid-like behaviour, including oils, greases, gels, foams, and the like. In this embodiment, the dielectric liquid medium is an oil. In this embodiment, the oil is of the same type as the above-mentioned lubricating/cooling oil in the compartments of the thruster 101.

In addition to the waveguide 401a, the wireless communication system 401 comprises a transmitter 401b and a receiver 401c which are respectively configured to transmit and receive the above-mentioned electromagnetic data signal. In this embodiment, the transmitter 401b comprises an antenna. In this embodiment, the antenna is a directional antenna, for example a flat panel directional antenna. In this embodiment the transmitter 401b is located outside the waveguide 401a proximate the lower end thereof. The position of the transmitter 401b relative to the waveguide 401a is selected such that the transmitter 401b can direct the electromagnetic data signal into the waveguide 401a. Preferably, the transmitter 401b is located directly below the waveguide 401a, or as close to this as possible depending on space constraints.

In this embodiment, the receiver 401c comprises an antenna. In this embodiment, the antenna is a directional antenna, for example a flat panel directional antenna. In this embodiment, the receiver 401c is located outside the waveguide 401a proximate the upper end thereof, and inside the gear compartment 301, which also contains lubricating/cooling oil. The position of the receiver 401c relative to the waveguide 401a is selected such that the receiver 401c can receive the electromagnetic data signal from the waveguide 401a. The receiver 401c is arranged to pass the electromagnetic data signal to the marine vessel via a wired or wireless connection (not shown), or alternatively via a non-metal port in the gear compartment 301 which will allow the signal to escape into the vessel.

In this embodiment, the thruster 101 is equipped with a transducer which is configured to measure at least one physical parameter of the thruster 101. In this embodiment, the transducer is a vibration sensor 401d which measures vibration in the thruster 101.

In this embodiment, the thruster 101 is also equipped with a power source which may power the transmitter 401b, the vibration sensor 401d, and/or processing/control system elements of the system, and may also provide recharging of a battery. In this embodiment, the power source is a thermoelectric generator 401e which is mounted to an internal surface of a wall of the thruster 101 and is configured to harvest power from a difference in temperature between the (relatively hotter) oil inside the thruster 101 and the (relatively cooler) water outside the thruster 101. The thermoelectric is described in more detail later herein. Typically, the temperature of the oil is about 55 to 90 degrees Celsius and the temperature of the water is about 4 to 20 degrees Celsius. In this embodiment, the power output of the thermoelectric generator 401e is in the range of about 0.1 to 5 Watts. In this embodiment, the power is transmitted from the thermoelectric generator 401e by electrical wiring.

The operation of the wireless communication system 401 will now be described. In this exemplary embodiment, the vibration sensor 401d detects vibration in the thruster 101 and sends an appropriate data signal to the transmitter 401b. The transmitter 401b transmits a corresponding radio frequency (RF) data signal into the waveguide 401a at an appropriate frequency to match the physical characteristics of the waveguide 401a. The data signal wave is propagated through the oil toward the upper end of the waveguide 401a, from where it exits the waveguide 401a and is picked up by the receiver 401c. The receiver 401c then passes the data signal to the vessel, where the data signal may be processed. Alternatively, the data signal may be processed at any stage prior to transmission to the vessel. Processing may include compressing, for example to characteristic data such as fast Fourier transforms, or if particular limits (e.g. temperatures) are exceeded.

The EM data signal wave propagates through the oil in the waveguide 401a in field configurations known as transverse electric (TE) and transverse magnetic (TM) modes. In the TE mode, the electric field is entirely transverse to the direction of propagation, with a component of the magnetic field in the direction of propagation. Conversely, in the TM mode, the magnetic field is entirely transverse to the direction of propagation, with a component of the electric field in the direction of propagation. In general, the number of possible modes increases with the frequency for a given size of waveguide. Each of the TE and TM modes has its own cut-off frequency, the mode with the lowest frequency being the "dominant mode".

The waveguide can propagate the data signals in single-mode or multi-mode. Protocol, frequency band and channels may be continuously adapted to suit the transmitting medium, waveguide material, liquid flow and temperature, in order to optimise performance in that environment. This optimisation can be performed using knowledge of the dielectric properties of the oil at a specific state (temperature, moisture, etc), whether based on prior knowledge or by means of measurements from sensors that determine these properties in real-time.

Single-mode waveguides are designed to carry only a single-mode propagation of a chosen wavelength of signal, whereas multi-mode waveguides are designed to carry two or more modes of that signal along the same media. The number of modes supported depends on the chosen frequency of the signal (i.e. wavelength), the refractive index and permittivity of the media, and the diameter of the waveguide. Multi-mode propagation will occur with waveguide diameters that correspond to a cut-off frequency above the frequency being used.

The waveguide 401a can be designed for optimal wireless signal transfer for a chosen frequency band of operation— this can be determined, in this example, through control of the internal diameter of the hollow vertical drive shaft 101g during manufacture. Optimal performance in terms of minimal attenuation, maximum link quality and maximum data transfer throughput can be achieved by selecting an internal diameter that coincides with the ideal, single-mode propagation mode known as TE11. This TE11 diameter in general occurs at the minimum diameter range for a given frequency that also takes into account the "guide wavelength" of the signal when propagating through oil, therefore can be numerically solved using conventional methods given the physical characteristics of a particular oil.

TE11 mode and TM01 mode are dominant modes that determine minimum and maximum waveguide dimensions for single-mode design. Ideally, maximum performance is achieved with single-mode propagation, where frequencyTE11<frequency<frequencyTM01. When transmitting a single-frequency wireless signal, a single-mode waveguide may be desirable because it allows a longer range/depth to be achieved through the waveguide for the same amount of source output power. This is because all the EM energy is focused and radiated within a single mode (one strong mode) as opposed to the same energy being spread out over two or more modes (several weaker modes). However, a single-mode waveguide for a primary frequency can also carry single or multi-mode signals from a secondary signal of higher frequency (i.e. shorter wavelength). Single-mode provides more concentrated energy within a single order, therefore is more energy efficient and enables a longer transmission distance particularly when transmitting through a relatively 'lossy' medium such as oil or fuel.

For 802.11b/g Wi-Fi in the 2.4 GHz band frequency range, TE11 and TM01 cut-off frequencies for the smallest waveguide diameter possible at 7.35 cm (rounded to the closest 0.5 mm) are 2390.45 MHz and 3122.25 MHz respectively. This comfortably envelopes the 2.4 GHz range between 2400-2483.5 MHz for optimum single-mode performance. The optimal metal waveguide diameter ranges from 7.35 cm to 9.2 cm before it transcends to multi-mode beyond the upper limit. For the 5 GHz band, this diameter is significantly smaller at between 3.5 cm and 4.0 cm. Based on this knowledge of TE11 and TM01, the data table below serves as a design guideline to waveguide dimensions for wireless RF signals in the relevant ISM radio bands. A 60 GHz case is not shown in the table, given its higher power requirements and very small waveguide; however it could be used and would have a waveguide diameter of roughly 3 mm.

| ISM Band | 433 MHz | 868/900 MHz | 2.4 GHz | 5 GHz |
|---|---|---|---|---|
| Category | UHF (300 MHz-3 GHz) | UHF (300 MHz-3 GHz) | UHF (300 MHz-3 GHz) | Microwave (>3 GHz) |
| Centre freq (Hz) | 433920000 | 868000000 | 2450000000 | 5500000000 |
| Min freq (Hz) | 433050000 | 779000000 | 2400000000 | 5180000000 |
| Max freq (Hz) | 434790000 | 928000000 | 2483500000 | 5825000000 |
| Wavelength - Centre (cm) | 69.089 cm | 34.538 cm | 12.236 cm | 5.4483 cm |
| Wavelength - Max | 69.228 cm | 38.484 cm | 12.491 cm | 5.7875 cm |
| Wavelength - Min | 68.951 cm | 32.305 cm | 12.071 cm | 5.1467 cm |
| Minimum pipe diameter where $freq_{TE11} < freq < freq_{TM01}$ | 40.6 cm | 22.5 cm | 7.35 cm | 3.5 cm |
| Corresponding TE11 mode cut-off freq, i.e. lower freq limit | 432.75 MHz | 781 MHz | 2390.45 MHz | 5019.95 MHz |
| Corresponding TM01 mode cut-off freq, i.e. upper freq limit | 565.23 MHz | 1020 MHz | 3122.25 MHz | 6556.72 MHz |

Since the waveguide 401a is used in a confined metal environment, it would be possible to use frequencies outside ISM bands to match the frequency to any diameter, though care would need to be taken to ensure the RF signals do not escape, for example using relays that turn off the wireless communication system 401 if a hatch of the thruster 101 is opened.

The terms "transmitter" and "receiver" are used herein to highlight that the wireless communication system 401 predominantly sends a data flow out of the thruster 101. However, as will be understood by the skilled reader, two-way communication can be used in wireless links, for example for error correction or "handshaking" (i.e. a signal sent to acknowledge successful receipt of data) or control of the wireless nodes. Thus, the transmitter and receiver are effectively transceivers and signals may be conveyed in either direction by the transmitter and receiver. Furthermore, the transmitter and/or receiver could send control data into the thruster 101, for example to electric motors, actuators, or to the health monitoring system, e.g. to take readings more often.

The waveguide 401a and/or the various compartments of the thruster 101 may comprise gas (e.g. air) as well as oil (or other liquid medium). In this case the EM data signal will propagate through the gas as well as the oil.

It will be understood that the above-mentioned vibration sensor is merely an example of a transducer or similar device which may be found in a health-monitoring or diagnostic system of a thruster, and which can provide useful data to be conveyed by the wireless communication system. Other examples include, but are not limited to, devices which detect temperature, torque, speed, acoustic noise, flow rates, and oil quality.

Figure 3:
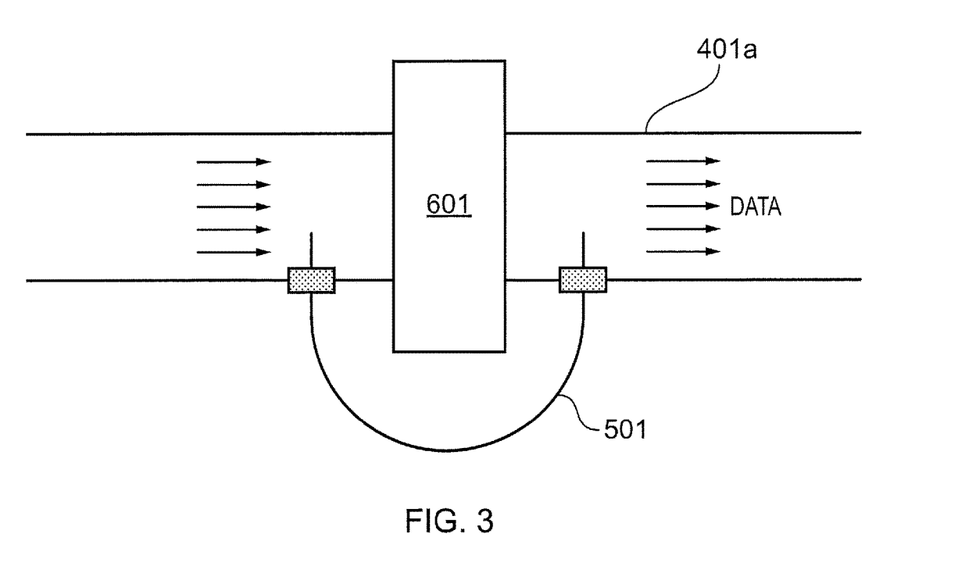
FIG. 3 shows a re-radiating element of the wireless communication system.

Referring now to FIG. 3, an embodiment includes a re-radiating element, or dielectric penetrator 501, which provides a bridge for the data signal across an obstacle 601 in the waveguide 401a which would otherwise present a "blockage" to the EM wave travelling through the waveguide 401a. Examples of such obstacles 601 include components such as filters, valves, pumps, heat exchangers, and the like. The dielectric penetrator 501 operates on the well-known "coaxial effect" and may also be used as a bridge between the upper, lower and middle portions 101*a*-*c* of the thruster 101. The dielectric penetrator 501 can further be used to pass the data signal through spaces in the thruster 101 having dimensions too narrow for TE11 and TM01 modes.

The data signal which is conveyed through the oil in the waveguide 401*a* may be utilised to identify a change in the quality of the oil. For example, any variation of signal transmission power required in certain conditions (e.g. oil at temperature X degrees requires power Y Watts, where Y is greater than usual) may indicate a deterioration in oil quality. A build-up of particulates in the oil could increase attenuation, which may be detected by a change in wireless transmission power required for a given signal strength received. Servicing may then be planned to forestall any associated problems. In particular, where the waveguide 401*a* is known to be completely filled with oil, and other factors effecting the wireless transmission (such as signal interference) are effectively eliminated by the waveguide design, the power required to transmit the data can be used to intrinsically measure oil quality without additional sensors.

In an embodiment, the electrically non-conductive medium in the waveguide is a solid material, for example a carbon composite material. In this case the waveguide and/or the thruster compartments may also comprise an electrically non-conductive gas medium (e.g. air) as has been described herein above.

In an embodiment, the waveguide has a generally rectangular cross-section, optionally a square cross-section.

In an embodiment, the waveguide comprises a pipe or tube which is arranged concentrically around and extends along at least a portion of a drive shaft of the marine propulsor.

In an embodiment, the waveguide comprises an existing component of the thruster, for example an oil pipe, a fuel pipe, or any other pipe-like or tubular structure which is suitable for conveying the data signal. Circular pipes have been shown to be similar to metal tube (hollow) waveguides. The well-known Bessel function can be used to identify the propagation constants, the different transverse electric and transverse magnetic modes, cut-off frequencies and multimode attenuation. Knowledge of these values can help to identify whether a pipe is useable and how well it will perform for a given wireless frequency range. Conversely, these parameters can be used to optimize or "tune" the specification of pipes in a thruster design to maximise their utility as waveguides. Generally, the higher the frequency used, the smaller the waveguide can be.

Figure 4A:
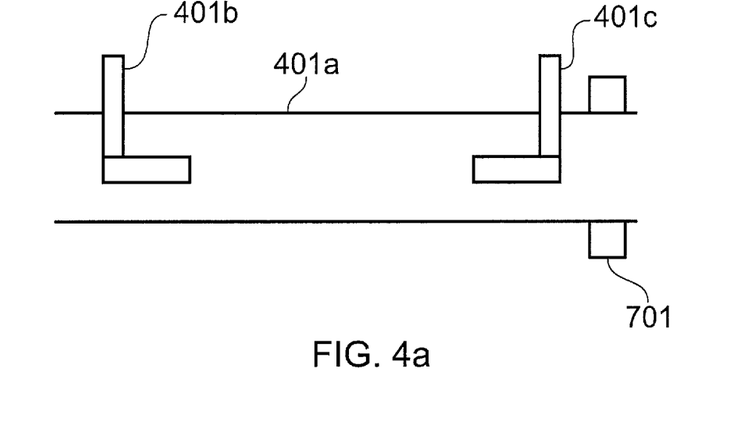
FIGS. 4a and 4b show possible configurations of transmitters and receivers of the wireless communication system.

In an embodiment illustrated in FIG. 4*a*, both of the transmitter 401*b* and the receiver 401*c* are located (completely or partially) inside the waveguide 401*a*. In another embodiment, the receiver is located (completely or partially) inside the waveguide and the transmitter is located outside the waveguide. In another embodiment, the transmitter is located (completely or partially) inside the waveguide and the receiver is located outside the waveguide.

In an embodiment, the transmitter and/or the receiver is integrally formed with the waveguide. For example, in the embodiment illustrated in FIG. 4*b* the transmitter 401*b* forms part of the tubular structure of the waveguide 401*a*.

In an embodiment, the transmitter and/or the receiver is a dipole antenna or a patch antenna.

Figure 4B:
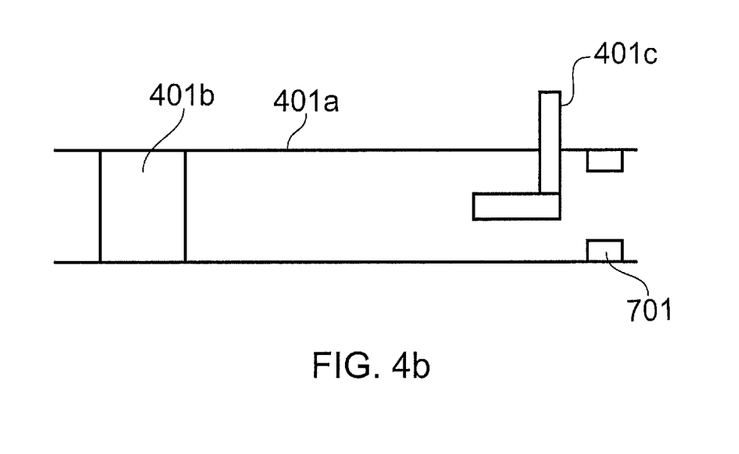

The embodiments of FIGS. 4*a* and 4*b* each include an optional EMI choke 701. As will be understood by the skilled reader, RF chokes may be used to remove noise. Typically, an inductor surrounds or "chokes" the transmission path (e.g. a cable) and prevents the signal from passing, like a filter. Essentially, inductance is created around the RF transmission; the more coils in the inductor (the choke), the lower the filter cut-off frequency. A similar effect could also be achieved by a reduction in pipe diameter, to cut off the waveguide effect.

In an embodiment, the waveguide includes reflectors for directing the data signal around tight bends or junctions of the waveguide.

In an embodiment, the power source for the wireless communication system is a battery. Alternatively, the power source may comprise an oil flow generator or a small shaft/gear/bearing generator.

While the wireless communication system has been described herein above with respect to a "Z-drive" marine thruster, it will be understood that other arrangements are possible, for example an "L-drive" in which the horizontal input shaft is omitted and the vertical drive shaft is driven directly, for example by an engine or a motor. The invention is also applicable to marine propulsors other than azimuth thrusters. Furthermore, the invention may be used in various other marine environments where signal propagation can be difficult around or through small, constrained (especially metal) spaces, such as ship compartments comprising watertight doors, ports or windows, where a suitable waveguide may be found or provided.

Figure 5:
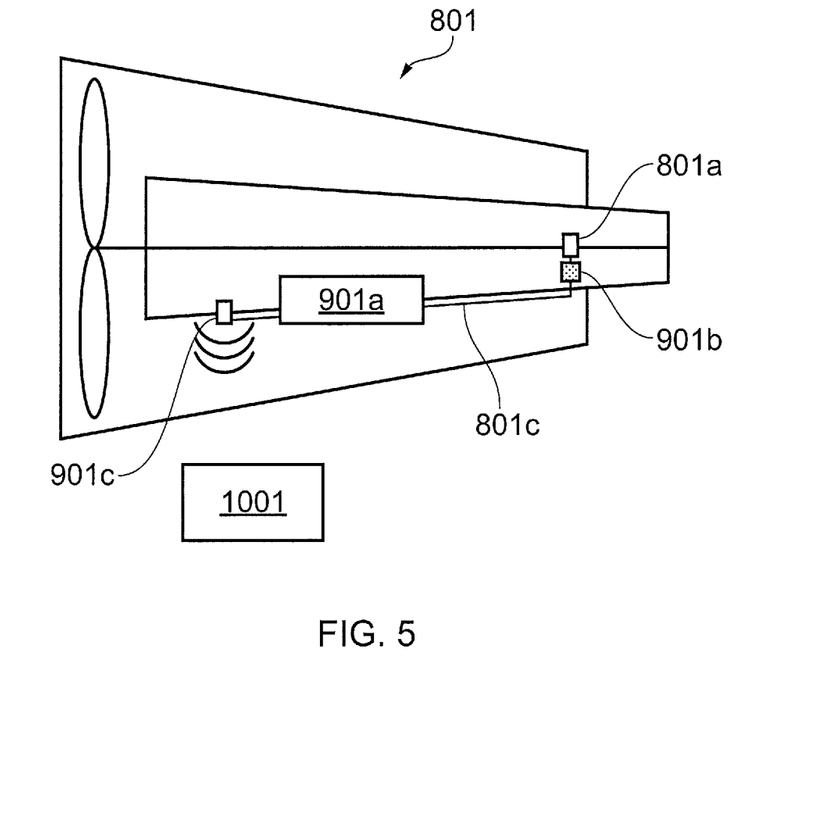
FIG. 5 shows a wireless communication system installed in a gas turbine engine.

The invention also has wider utility, including in enclosed spaces such as oil or fuel tanks, (gas turbine) engines, and gearboxes, as may be found in various industries including aviation, automotive, and (nuclear) power generation. For example, referring to FIG. 5 there is shown a gas turbine engine 801 comprising a shaft bearing 801*a* which is fed with oil from an oil pump 801*b* via an oil pipe. In this embodiment, the oil pipe (which may be a scavenge or a fully pressurised pipe) comprises a waveguide 901*a*. The bearing 801*a* is equipped with a vibration sensor (not shown) which is arranged to send data to a transmitter 901*b*, from which a data signal is transmitted through the waveguide 901*a* to a receiver 901*c* and then on to a health monitoring unit 1001 of the engine 801. Utilising the existing oil pipe as a waveguide avoids the need to run wires or cables for carrying the data signal.

Figure 6:
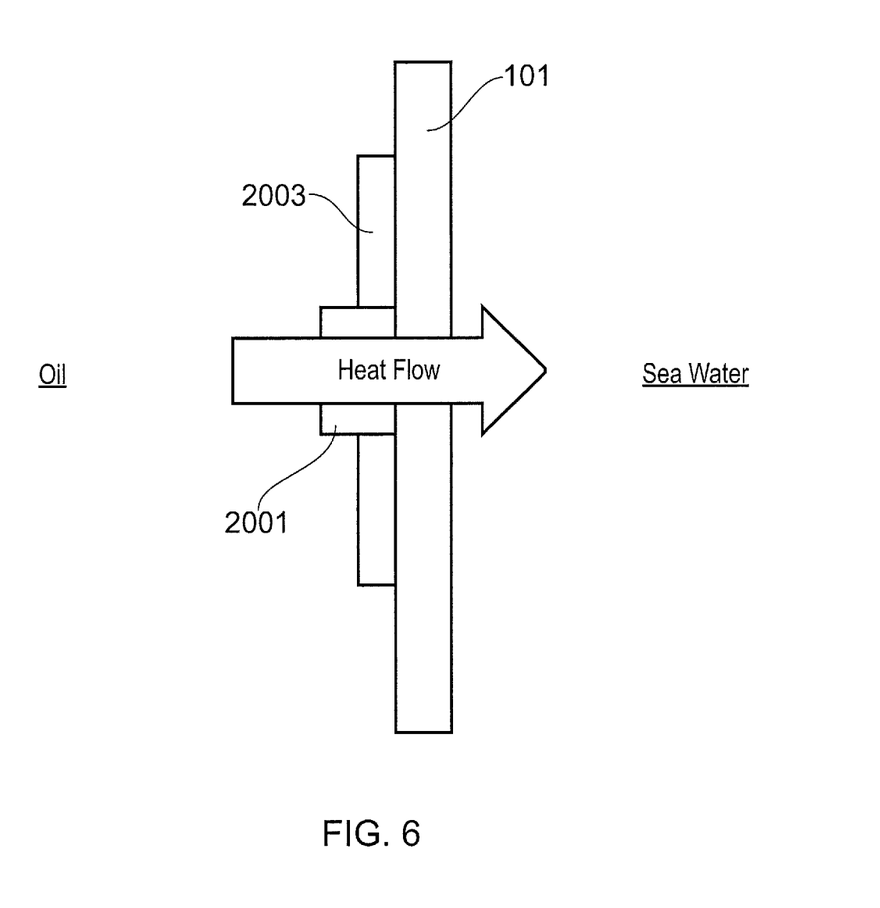
FIG. 6 shows a thermoelectric element of the wireless communication system.

With reference to FIG. 6, a thermoelectric 2001 is a solid state semiconductor device that converts a sustained temperature difference over its two sides into electrical power. Heat essentially flows through the device, with a proportion of that heat converted into electrical power (i.e. more heat will flow into the device than out of it). The device uses an effect known as the Seebeck Effect, where the heat on one side excites carriers (electrons or holes depending on whether it is a p-type or n-type semiconductor), creating carrier diffusion, which leads to a concentration of carriers in one half of the semiconductor. The carriers have a charge, therefore a voltage difference is built up, and using both a p-type and n-type semiconductor together, electrical power can be generated.

The thermoelectric 2001 may include heat exchangers (not shown) to ensure low thermal resistance between the heat source (hot oil) and the thermoelectric 2001. The heat exchangers may be larger than the thermoelectric 2001, and therefore a heat spreader (such as copper) may be used. Cold thermal contact between all layers ensures that heat flows through the thermoelectric 2001. This includes the contact with the wall of the thruster 101, to ensure that good contact is made with the cold sea water. Contact means may include high pressure clamping, for example using malleable pastes or gels, or soft metal alloys (i.e. metals with good thermal conductivity, but that are also compressible, enabling a good thermal contact to be made).

The thermoelectric needs a hot and cold source. To ensure that the cold sea water can impact the thermoelectric 2001, a cold spot may be provided by thermal insulation 2003 at the area surrounding the thermoelectric 2001. This prevents the hot oil from heating the wall of the thruster 101 in the vicinity of the thermoelectric 2001. By extending the area and thickness of the insulation 2003 surrounding the thermoelectric 2001, the thermal resistance to the cold spot in the wall of the thruster 101, to which the thermoelectric 2001 is connected, increases. This ensures a temperature difference between the oil and sea water is maintained.

It will be understood that the invention has been described in relation to its preferred embodiments and may be modified in many different ways without departing from the scope of the invention as defined by the accompanying claims. Furthermore, the skilled reader will understand that the features of the invention as described herein may be arranged in any appropriate combination in the context of its different uses.

The invention claimed is:

1. A marine propulsor comprising a wireless communication system, the wireless communication system comprising:
    a transmitter;
    a receiver; and
    a drive shaft defining a hollow interior, the hollow interior comprising a waveguide, arranged to convey an electromagnetic data signal between the transmitter and the receiver;
    wherein the waveguide comprises an electrically non-conductive solid or liquid medium for propagating the electromagnetic data signal.

2. The marine propulsor according to claim 1, wherein the electrically non-conductive medium is a liquid comprising an oil, a grease, a gel, a foam, a fuel, or a hydrocarbon fuel.

3. The marine propulsor according to claim 1, wherein the waveguide is configured for multi-mode wave propagation.

4. The marine propulsor according to claim 1, wherein the waveguide is configured for single-mode wave propagation.

5. The marine propulsor according to claim 1, wherein the receiver and the transmitter are disposed at least partially in the waveguide, or wherein one of the receiver and the transmitter is disposed at least partially in the waveguide and the other of the receiver and the transmitter is disposed out of the waveguide, or wherein the receiver and the transmitter are disposed out of the waveguide.

6. The marine propulsor according to claim 1, wherein the waveguide is constructed from a metal or a metal alloy.

7. The marine propulsor according to claim 1, wherein the waveguide has a generally circular cross-section, or wherein the waveguide has a generally rectangular cross-section.

8. The marine propulsor according to claim 1, wherein one or both of the receiver and the transmitter is integrally formed with and a part of the waveguide.

9. The marine propulsor according to claim 1, including a thermoelectric generator configured to power the wireless communication system.

10. The marine propulsor according to claim 9, wherein the thermoelectric generator is configured to generate power using a temperature difference between a liquid inside the marine propulsor and water outside the marine propulsor.

11. The marine propulsor according to claim 10, wherein the liquid inside the marine propulsor is of the same type as the electrically non-conductive liquid medium for conveying the electromagnetic data signal.

12. The marine propulsor according to claim 1, including a sensor which is configured to detect a physical parameter of the marine propulsor, the electromagnetic data signal corresponding to the physical parameter.

13. The marine propulsor according to claim 12, wherein the sensor is a vibration sensor.

14. The marine propulsor according to claim 1, including a re-radiating element for bridging around an obstacle or a space in the propulsor to convey the electromagnetic data signal.

15. The marine propulsor according to claim 1, wherein the waveguide comprises a conventional liquid-containing component of the marine propulsor.

16. A method of operating a wireless communication system according to claim 1, the method comprising:
    determining dielectric properties of the solid or liquid medium;
    propagating the electromagnetic data signal; and
    adapting protocol, frequency and/or channels to suit the dielectric properties in order to optimise the quality of the electromagnetic data signal.

17. A method of determining a change in the quality of an oil in a marine propulsor, comprising the steps: providing a marine propulsor with a wireless communication system, the wireless communication system comprising a transmitter; a receiver; and a waveguide arranged to convey an electromagnetic data signal between the transmitter and the receiver, the waveguide comprising an electrically non-conductive oil for propagating the electromagnetic data signal; monitoring a power required by the transmitter to convey the electromagnetic data signal; and identifying a change in the required power which is indicative of a change in the quality of the oil.

18. The marine propulsor according to claim 1, further comprising an upper portion, an elongate middle portion, and a lower portion including a propeller, the upper portion and the lower portion being separated from the middle portion by internal dividing structural walls, the drive shaft extending within the upper portion, the middle portion and the lower portion.

19. The method of claim 17, further comprising:
    determining the change in the quality of the oil based on the change in the required power.

* * * * *